US011099385B2

(12) United States Patent
Zhou et al.

(10) Patent No.: US 11,099,385 B2
(45) Date of Patent: Aug. 24, 2021

(54) VIRTUAL REALITY (VR) SYSTEM WITH NEARSIGHTEDNESS OPTOMETRY ADJUSTMENT

(71) Applicant: Intel Corporation, Santa Clara, CA (US)

(72) Inventors: Zhen Zhou, Shanghai (CN); Yu Yu, Shanghai (CN); Ke Han, Shanghai (CN)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/579,593

(22) PCT Filed: Dec. 30, 2016

(86) PCT No.: PCT/IB2016/058089
§ 371 (c)(1),
(2) Date: Jul. 10, 2019

(87) PCT Pub. No.: WO2018/122580
PCT Pub. Date: Jul. 5, 2018

(65) Prior Publication Data
US 2020/0124852 A1    Apr. 23, 2020

(51) Int. Cl.
*G02B 27/01* (2006.01)
*G02C 7/08* (2006.01)
(Continued)

(52) U.S. Cl.
CPC ............ *G02B 27/0172* (2013.01); *A61B 3/02* (2013.01); *A61B 3/1035* (2013.01);
(Continued)

(58) Field of Classification Search
CPC ............ G02B 27/0172; G02B 27/0176; G02B 2027/0134; G02B 2027/0136;
(Continued)

(56) References Cited

U.S. PATENT DOCUMENTS

2012/0236257 A1* 9/2012 Hillis .................... A61B 3/0025
351/205
2014/0132485 A1* 5/2014 Kim .................... G02B 27/0172
345/8
(Continued)

FOREIGN PATENT DOCUMENTS

JP          3397832 B2 *  4/2003
JP          3397832 B2 *  4/2003
WO       2016115285 A1    7/2016

OTHER PUBLICATIONS

International Search Report and Written Opinion for PCT Patent Application No. PCT/IB2016/058089, dated Sep. 19, 2017, 12 pages.

*Primary Examiner* — Brent D Castiaux
(74) *Attorney, Agent, or Firm* — Compass IP Law PC

(57) ABSTRACT

A virtual reality headset system includes a vision correction module. The vision correction system can detect a degree of myopia or other visual ailment of a user of the VR system, and then adjust a vision correction lens to adjust for user myopia. An implementation of the vision correction module can adjust right and left lenses separately.

14 Claims, 5 Drawing Sheets

(51) Int. Cl.
*A61B 3/103* (2006.01)
*A61B 3/00* (2006.01)
*A61B 3/02* (2006.01)
*G06T 19/00* (2011.01)

(52) U.S. Cl.
CPC ......... *G02B 27/0176* (2013.01); *G02C 7/081* (2013.01); *G06T 19/006* (2013.01); *A61B 3/00* (2013.01); *G02B 2027/0134* (2013.01); *G02B 2027/0136* (2013.01)

(58) Field of Classification Search
CPC .... G02B 2027/0181; G02B 2027/0154; A61B 3/1035; A61B 3/02; A61B 3/00; A61B 3/10; A61B 3/103; A61B 3/18; G02C 7/081; G06T 19/006
See application file for complete search history.

(56) References Cited

U.S. PATENT DOCUMENTS

2016/0066780 A1* 3/2016 Pamplona ............ A61B 3/0025
351/206
2016/0178912 A1   6/2016 Kusuda et al.
2016/0363770 A1* 12/2016 Kim ........................ A61B 3/10

* cited by examiner

VIRTUAL REALITY (VR) SYSTEM WITH NEARSIGHTEDNESS OPTOMETRY ADJUSTMENT

CLAIM OF PRIORITY

This application is a U.S. National Phase application under 35 U.S.C. § 371 of International Application No. PCT/IB16/58089, filed Dec. 30, 2016, entitled "VIRTUAL REALITY (VR) SYSTEM WITH NEARSIGHTEDNESS OPTOMETRY ADJUSTMENT" the entire contents of which are incorporated herein by reference.

FIELD

Descriptions herein are generally related to virtual reality (VR) systems, and more particular descriptions are directed to a VR system that adjusts for visual impairment.

COPYRIGHT NOTICE/PERMISSION

Portions of the disclosure of this patent document may contain material that is subject to copyright protection. The copyright owner has no objection to the reproduction by anyone of the patent document or the patent disclosure as it appears in the Patent and Trademark Office patent file or records, but otherwise reserves all copyright rights whatsoever. The copyright notice applies to all data as described below, and in the accompanying drawings hereto, as well as to any software described below: Copyright© 2016, Intel Corporation, All Rights Reserved.

BACKGROUND

Nearsightedness is the most common ailment in the world. More than 1 in four people worldwide are estimated to suffer from nearsightedness or myopia. Some places have higher incidence of the condition than others. For example, it is estimated that approximately 40% of the total population of the People's Republic of China has myopia. While there are many vision correction options for people with myopia, for a very significant number of those people with myopia, glasses are the best option. However, glasses are not generally compatible with virtual reality (VR) headsets.

While there are a significant number of handheld VR systems and VR headsets on the market, the current options for dealing with myopia are mechanical adjustments, such as adjusting the distance of a VR screen to the user's eyes, using a mechanical gear that the user turns, or having a user choose and plug in adjustment lenses into the VR system. Manual adjustment based on current options results in deviation from proper correction. Additionally, the setup and overall user experience suffers as a result of requiring manual adjustments. Finally, the current adjustment mechanisms often result in reduced comfort (e.g., pressure or pain or eye strain or other discomfort) for the user, or can result in scratches on a user's glasses or the VR headset lens or both.

BRIEF DESCRIPTION OF THE DRAWINGS

The following description includes discussion of figures having illustrations given by way of example of implementations of embodiments of the invention. The drawings should be understood by way of example, and not by way of limitation. As used herein, references to one or more "embodiments" are to be understood as describing a particular feature, structure, and/or characteristic included in at least one implementation of the invention. Thus, phrases such as "in one embodiment" or "in an alternate embodiment" appearing herein describe various embodiments and implementations of the invention, and do not necessarily all refer to the same embodiment. However, they are also not necessarily mutually exclusive.

Descriptions of certain details and implementations follow, including a description of the figures, which may depict some or all of the embodiments described below, as well as discussing other potential embodiments or implementations of the inventive concepts presented herein.

DETAILED DESCRIPTION

As described herein, a virtual reality (VR) headset system includes a vision correction module. The vision correction system can detect a degree of myopia of a user of the VR system, and then adjust a vision correction lens to adjust for user myopia. An implementation of the vision correction module can adjust right and left lenses separately. A VR system can include additional elements compared to traditional systems. Namely, the VR system can include one or more elements to detect a need for vision correction, and one or more elements to apply vision correction.

Descriptions throughout refer to myopia or nearsightedness. Seeing that nearsightedness is a most common vision ailment, examples and descriptions are made in reference to myopia. However, the vision correction is not limited to correction for myopia. In one embodiment, vision correction can include correction for myopia. In one embodiment, vision correction can include correction for hyperopia. In one embodiment, vision correction can include correction for amblyopia. In one embodiment, vision correction can include correction for presbyopia. In one embodiment, the vision correction can include correction for a combination of these. Thus, it will be understood that vision correction operations that include an adjustment of one or more lenses can refer to an adjustment of the lenses to adjustment or movement for purposes of vision correction for any of these conditions or a combination.

Figure 1:
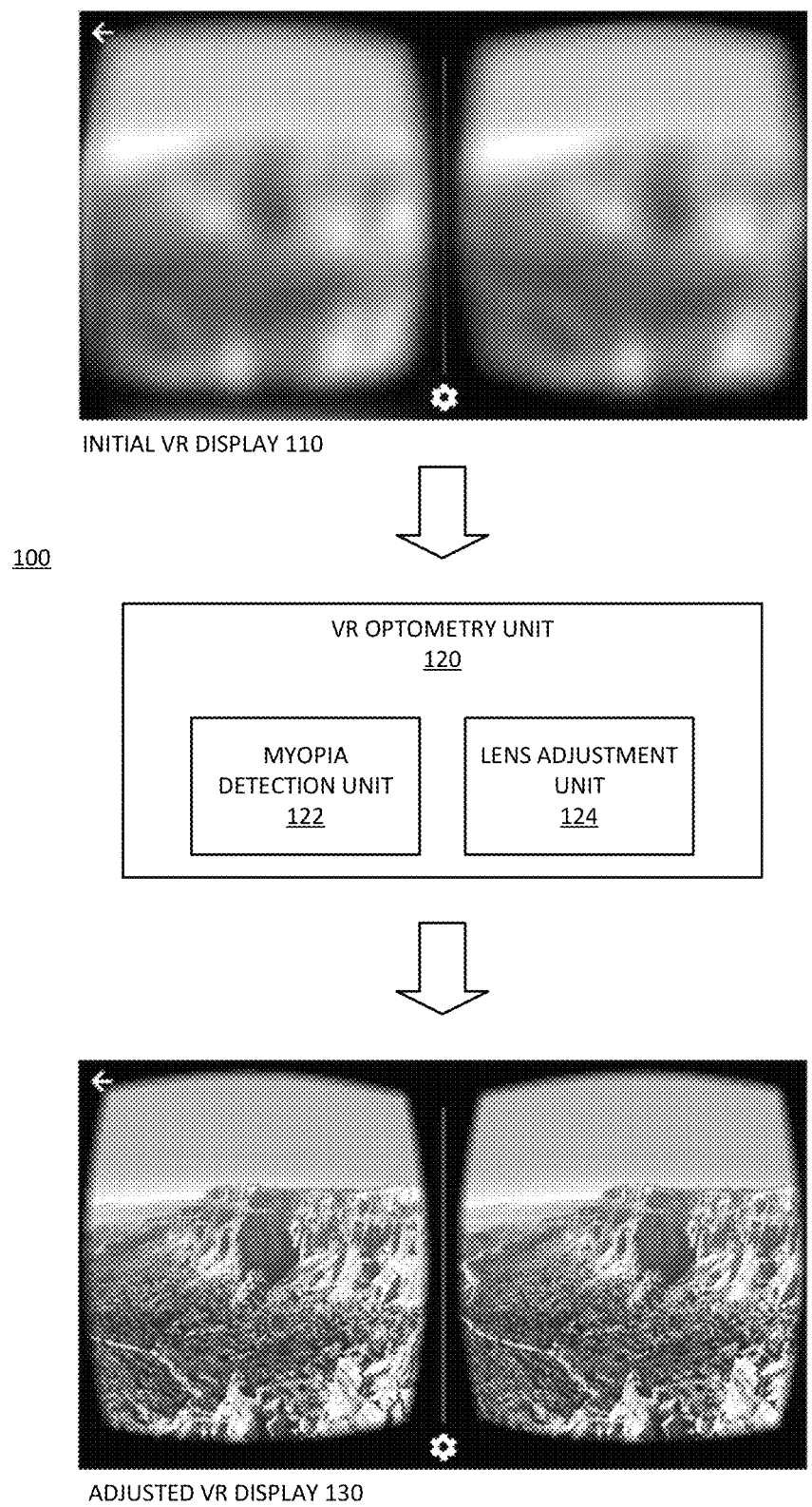
FIG. 1 is a representation of an embodiment of a system to provide vision correction in a virtual reality headset system.

FIG. 1 is a representation of an embodiment of a system to provide vision correction in a virtual reality headset system. System 100 includes VR optometry unit 120. In one embodiment, optometry unit 120 includes myopia detection unit 122 and lens adjustment unit 124. Myopia detection unit 122 enables system 100 to detect a specific degree of myopia for a user. Lens adjustment unit 124 enables system 100 to provide a specific, automatic adjustment of a lens to provide vision correction for the user while engaging with the VR display.

With system 100, a VR system that would initially appear blurry and unfocused to a user with myopia, as in initial VR display 110. Display 110 represents an uncorrected display for a user with nearsightedness. After application of vision correction as detected and applied by system 100, the same display appears as adjusted VR display 130. Display 130 represents a clear, focused display for the same nearsighted user, based on a vision correction adjustment of system 100.

Myopia detection unit 122 represents one or more components built into a VR system to detect whether or not a user has nearsightedness or myopia. Myopia detection unit 122 can determine a degree of nearsightedness for the specific user. In one embodiment, myopia detection unit 122 initiates operation automatically when a user initiates the VR system. In one embodiment, myopia detection unit 122 initiates in response to a request by a user to provide automatic vision correction. In one embodiment, myopia detection unit 122 includes an infrared (IR) unit to provide an IR signal to a user's eye and measure reflections. Based on an amount of light reflected, myopia detection unit 122 can compute a level of focus for the user, which can indicate whether the user has myopia and what degree of myopia the user has.

Lens adjustment unit 124 represents one or more components built into a VR system to perform a vision correction adjustment as detected by myopia detection unit 122. Lens adjustment unit 124 can automatically apply an adjustment for vision correction in response to detected myopia, whether myopia detection unit 122 initiates automatically or whether a user initiates myopia detection unit 122. The automatic application of an adjustment includes movement of a lens of the VR system to change the focus of light from a display in accordance with the detected degree of myopia. In one embodiment, the lens to be adjusted is a second VR system lens, which provides vision correction.

Figure 2:
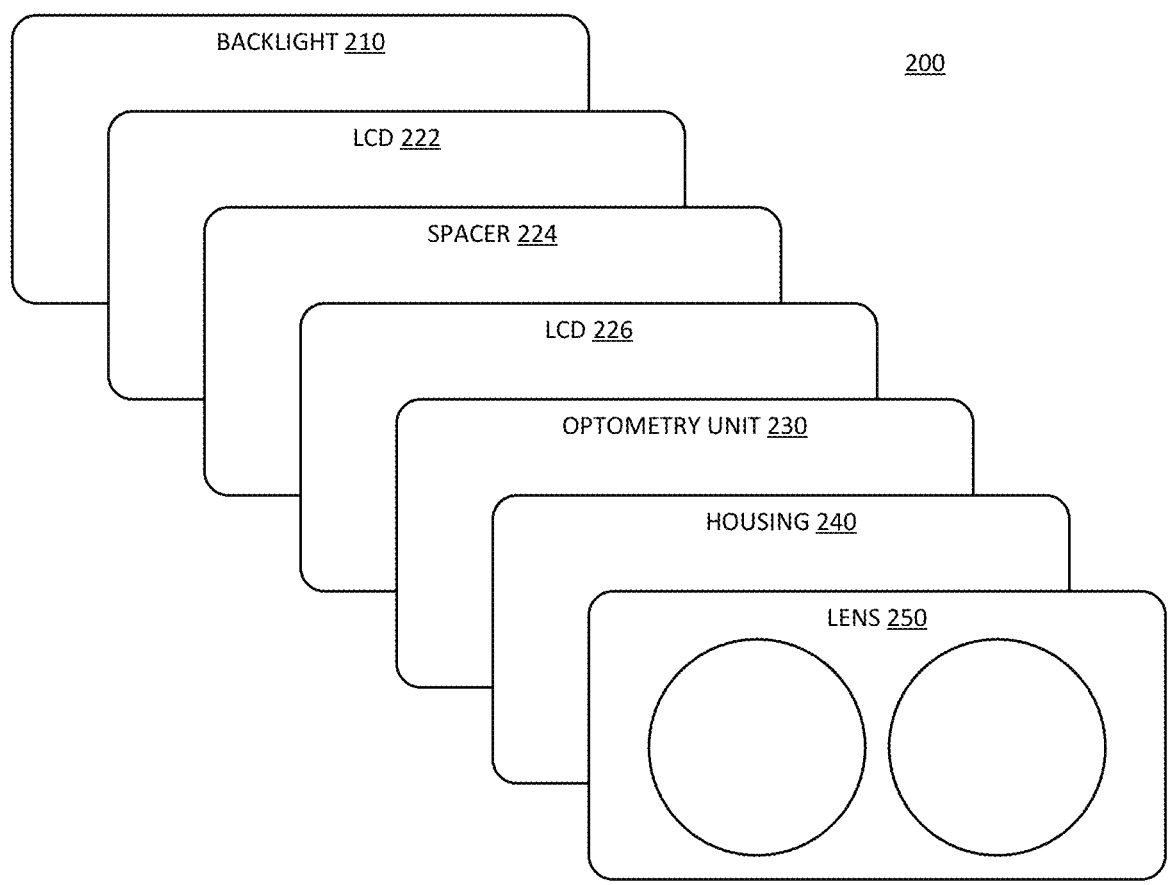
FIG. 2 is a block diagram of an embodiment of layers of a virtual reality system including a vision correction layer.

FIG. 2 is a block diagram of an embodiment of layers of a virtual reality system including a vision correction layer. System 200 provides one example of a system in accordance with system 100 of FIG. 1. More specifically, optometry unit 230 of system 200 can be an example of VR optometry unit 120.

System 200 includes housing 240 with lens 250. Housing 240 represents a housing system to position a VR display in front of a user's eyes to provide a VR display for VR interaction. Lens 250 represents one or more lens pieces to mount in housing 240, to provide the VR experience. The VR experience can be for gaming or learning or other experiences. Whether a single piece or multiple pieces, lens 250 provides focal functions for both eyes, as represented by the two separate circles.

Housing 240 includes a mount to receive a VR display source. In one embodiment, the mount includes mechanical and electrical connections for an integrated VR display device. For example, the VR display can include backlight 210 and one or more LCD (liquid crystal display) components. As illustrated in system 200, the VR source can include LCD 222 in front of backlight 210, with spacer 224 between LCD 222 and another LCD 226. The layered LCD displays can provide depth perception for a user. In one embodiment, the mount can include a mount to receive a mobile phone or other mobile device as the VR display device. In such an embodiment, system 200 excludes LCD display 222 or LCD display 226 or both. Additionally, the mobile device can operate as backlight 210.

In one embodiment, optometry unit 230 includes both a focus monitoring unit and a micromechanical control unit (not specifically shown). The focus monitoring unit provides myopia detection. The micromechanical control unit can be or be included in a vision correction unit. In one embodiment, optometry unit 230 includes one or more lens components (not specifically shown). With optometry unit 230, system 200 can be referred to as a "nearsightedness friendly" VR device, which can automatically adapt to different users, whether or not the user is myopic. In one embodiment, optometry unit 230 adjusts myopia separately for separate eyes, and thus can adjust precisely for different degrees of myopia for the separate eyes.

Optometry unit 230 includes hardware, such as motor control hardware, to adjust a lens position to provide vision correction. In one embodiment, optometry unit 230 includes a lens that is adjusted by a motor and motor control of optometry unit 230. In one embodiment, optometry unit 230 includes at least motor control to adjust a position of lens 250. In one embodiment, optometry unit 230 is at least partially integrated with lens 250. In one embodiment, only lens 250 moves within system 200. In one embodiment, lens 250 is stationary within housing or VR frame 240, and system 200 includes an additional, movable lens. Thus, system 200 includes an adjustable lens to move to provide vision correction.

Figure 3:
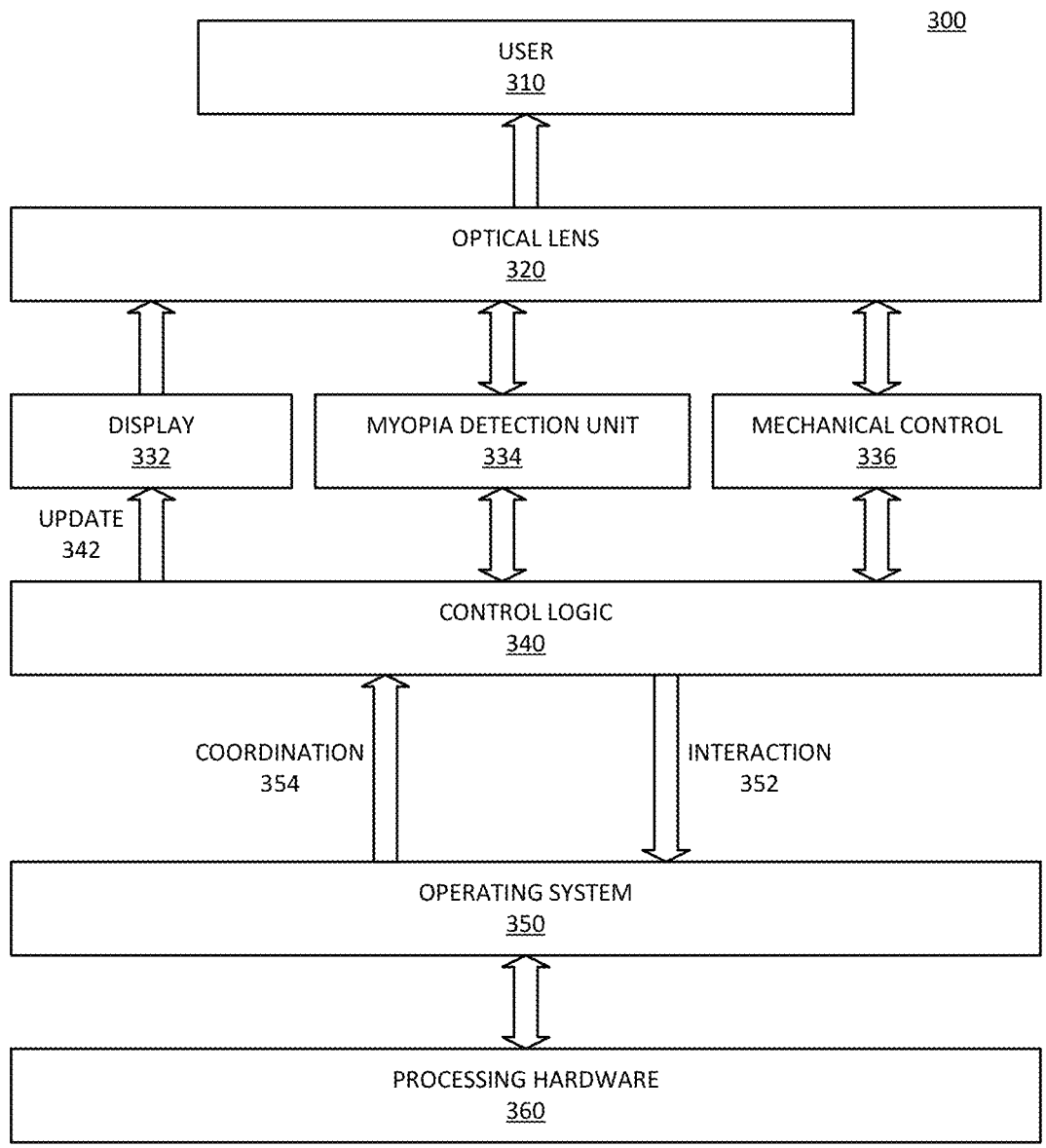
FIG. 3 is a block diagram of an embodiment of a virtual reality system with vision correction.

FIG. 3 is a block diagram of an embodiment of a virtual reality system with vision correction. System 300 provides one example of a VR system in accordance with system 200 of FIG. 2. User 310 represents a human user who uses the VR system. Typically, such a system mounts on the head of user 310, such as with straps or a head piece or other mechanical mount. User 310 looks into a VR system such as a headset towards a VR display source. The display source includes hardware to generate the VR images, and a display to present the images to user 310.

System 300 includes processing hardware 360, which represents one or more processing devices, such as microprocessors or graphics processors or both to compute images for a VR experience. Processing hardware 360 represents a hardware platform for system 300, and can include the main processing components as well as other components to receive input and provide interaction with user 310. In one embodiment, the hardware platform includes physical I/O (input/output) sources. In one embodiment, user 310 interacts with processing hardware 360 via one or more wireless links.

Operating system 350 represents software control for system 300, and executes on processing hardware 360. Operating system 350 represents the software platform for system 300. The hardware platform enables mechanical, physical, and wireless interaction with the VR experience. The software platform provides the programming or code for the processing systems to receive and interpret the input. In one embodiment, one or more processing elements can be implemented in logic arrays or other programmable hardware devices, which combine elements of hardware and software.

Operating system 350 receives interaction 352 from user 310, and provides coordination controls 354 to control logic 340 based on interaction 352. In one embodiment, control logic 340 can be considered part of the hardware platform. In one embodiment, control logic 340 can include hardware components. In one embodiment, control logic 340 can include software components. In one embodiment, control logic 340 can include firmware components. In one embodiment, control logic 340 can include a combination of hardware, software, or firmware components. Control logic 340 can include drivers to affect the display and interaction controls of system 300 for user 310.

System 300 includes display 332 to provide a VR display for user 310. Display 332 provides images through which a user experiences the VR scenario. Update 342 represents updates to the VR display based on interaction 352 and processing by processing hardware 360 and control logic 340. System 300 includes optical lens 310, which represents optics through which display 332 presents a VR experience to user 310.

In one embodiment, system 300 includes myopia detection unit 334, which can be a vision detection or focus detection system in accordance with any embodiment described herein. Myopia detection unit 334 provides mechanisms to determine if user 310 has myopia, and if so, what correction can be applied for it. The arrow from myopia detection unit 334 to optical lens 320 represents an embodiment where myopia detection unit 334 sends a light beam into the eyes of user 310 to detect myopia, and receives reflections based on the light beam. In one embodiment, myopia detection unit 334 includes an infrared sensor and a focus monitoring unit to detect a degree of myopia of each of the user's eyes.

In one embodiment, system 300 includes mechanical control 336 to provide adjustment to a movable optical lens 320. Optical lens 320 can represent multiple lenses, one or more of which is adjustable, while one or more others may not be adjustable. Mechanical control 336 can adjust one or more optical lenses 320 automatically, meaning a user does not need to manually adjust lens positions. The arrow from mechanical control 336 represents control signals provided to a motor or control operations provided by a motor to adjust optical lens 320, and a feedback signal to allow precise adjustment of the movement of the lens to provide the correction focus to adjust for vision impairment of user 310.

Figure 4:
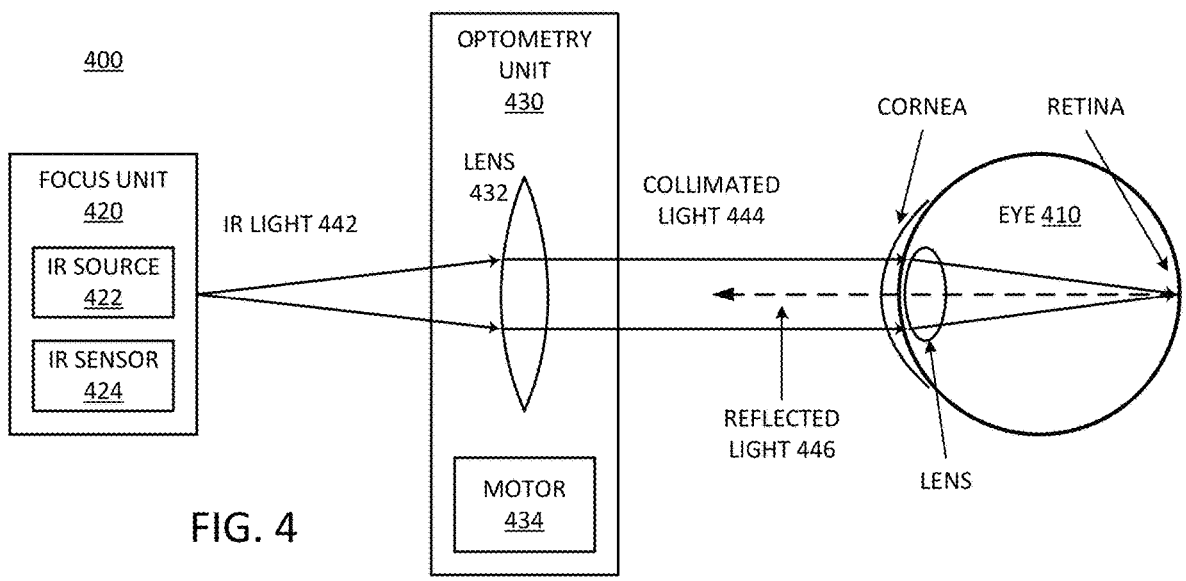
FIG. 4 is a diagrammatic representation of an embodiment of focus detection to detect a degree of myopia.

FIG. 4 is a diagrammatic representation of an embodiment of focus detection to detect a degree of myopia. System 400 provides an example of elements of a myopia detection unit in accordance with system 100, system 200, system 300, or a combination. System 400 includes focus unit 420 and optometry unit 430 to perform operations to detect the proper vision correction for eye 410 of a user. In one embodiment, system 400 represents a vision correction system for a single eye (right or left eye), and a same or similar system provides vision correction for the other eye.

Focus unit 420 enables system 400 to measure a focal distance that will provide correct focus on the retina of eye 410. In one embodiment, focus unit 420 generates IR light 442 with IR source 422 and emits IR light 442 through optometry unit 430. Optometry unit 430 includes lens 432, which collimates and directs collimated light 444 to eye 410. The light passes through the cornea and is focused by the eye lens to the retina. In myopic individuals, the light will not converge on the retina. The amount of reflected light 446 indicates how focused the light is on the retina.

In one embodiment, focus unit 420 includes a received or reflected light path to receive reflected light 446 with IR sensor 424. In one embodiment, optometry unit 430 includes a filter to redirect reflected light 446 to a detector or IR sensor external without passing back through lens 432. Thus, IR sensor 424 may be on either side of lens 432. In either case, system 400 includes a detector to receive reflected light 446 and send a light detection signal to a processor. The light detection signal can include a value representing an amount of reflected light. Based on the value, a processor of system 400 computes a proper position of lens 432 to focus IR light 442 on the retina.

In one embodiment, focus unit 420 emits the light and measures reflected light 446, and then adjusts a position of lens 432 to determine what difference exists in the amount of reflected light 446. System 400 can iteratively continue the process to detect a maximum amount of reflected light, for example. In one embodiment, optometry unit 430 includes motor 434, which receives one or more control signals (e.g., from focus unit 420 or other control logic or control unit) to adjust a position of lens 432. In one embodiment, motor 434 represents a micromechanical control unit. In one embodiment, the micromechanical control unit includes a micro axis stepper motor and motor driver.

In one embodiment, focus unit 420 initiates detection of myopia in response to a user initiating the VR system. In one embodiment, focus unit 420 initiates detection of myopia in response to a request or command by the user. In one embodiment, focus unit 420 initiates adjustment of a lens for a VR interaction in response to detection of myopia. In one embodiment, focus unit 420 adjusts the lens in the process of detecting myopia, and maintains the lens in the position detected to provide the best focus of light on eye 410. In one embodiment, after automatic adjustment of lens 432 by optometry unit 430 or focus unit 420 or both, a user can request additional adjustment of the vision correction.

Again, as mentioned above, descriptions related to myopia are not limited. In one embodiment, system 400 can detect and adjust any one or more of vision ailments, including but not limited to myopia, hyperopia, amblyopia, presbyopia, or a combination.

Figure 5:
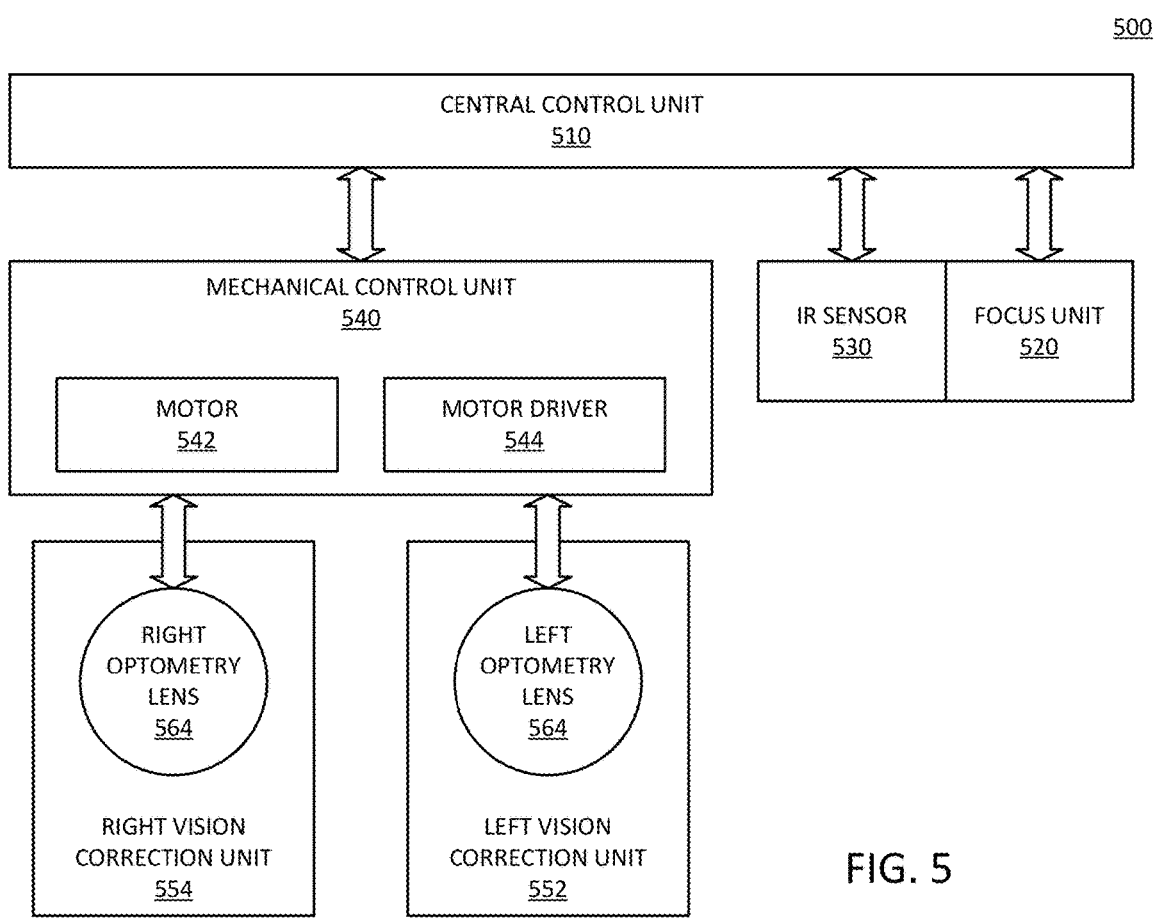
FIG. 5 is a block of an embodiment of a vision correction system for a virtual reality headset.

FIG. 5 is a block of an embodiment of a vision correction system for a virtual reality headset. System 500 provides one example of a system in accordance with system 100, system 200, system 300, system 400, or a combination. System 500 illustrates an embodiment of a vision correction system for a VR unit that includes separate control for right and left eyes.

In one embodiment, system 500 includes central control unit 510, which can control IR sensor 530 to send a beam of infrared light to each eye of the user and receive the feedback of infrared reflection. In one embodiment, focus unit 520 represents a focus monitoring unit that can adjust and repeat the sending of IR and receiving feedback determine a myopic degree of each eye individually. In one embodiment, IR sensor 530 is part of focus unit 520.

In one embodiment, central control unit 510 controls mechanical control unit 540. In one embodiment, mechanical control unit 540 includes motor 542 and motor driver 544. In one embodiment, motor 542 is or includes a stepper motor. Mechanical control unit 540 can be referred to as a micromechanical control unit, which controls both left and right optometry to adapt different myopic degree of each eye of the user.

As illustrated, mechanical control unit 540 can adjust a position of right optometry lens 564 of right vision correction unit 554 for right eye vision correction. Mechanical control unit 540 can adjust a position of left optometry lens 562 of left vision correction unit 552 for left eye vision correction. In one embodiment, mechanical control unit 540 includes separate motors or separate control units or both to separately adjust left and right vision correction. It will be understood that for separate left and right vision correction in system 500, focus unit 520 includes separate focus detection for left and right eyes.

Figure 6:
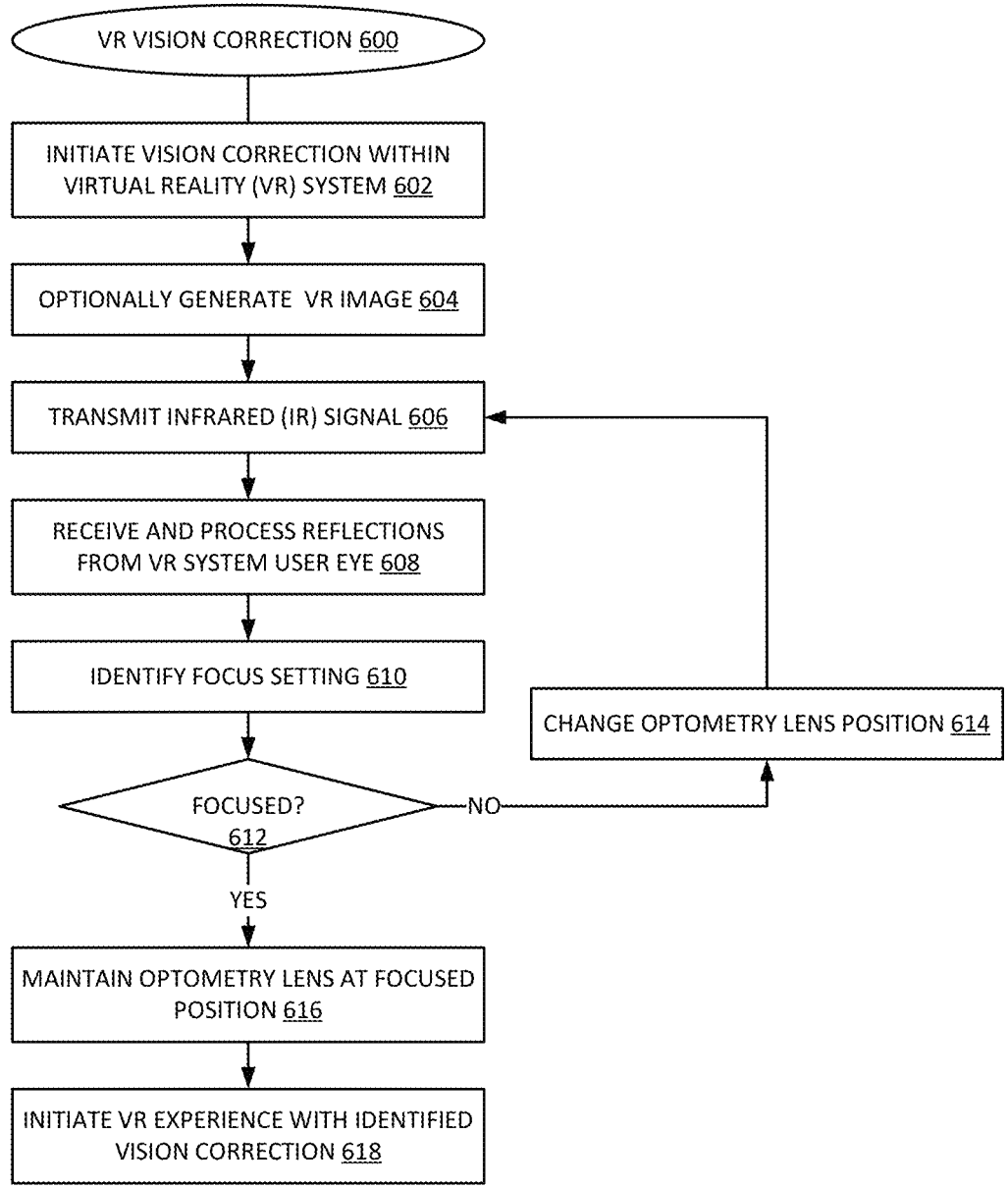
FIG. 6 is a flow diagram of an embodiment of a process for virtual reality vision correction.

FIG. 6 is a flow diagram of an embodiment of a process for virtual reality vision correction. Process 600 provides an example of a process for virtual reality unit vision correction in accordance with an embodiment of a virtual reality unit.

The vision correction unit initiates vision correction operations within the VR system, 602. In one embodiment, the vision correction unit initiates in response to a unit signal or command. In one embodiment, the vision correction unit initiates automatically, such as in response to initiation of the VR system. In one embodiment, the VR system optionally generates an IR image for display during vision correction, 604. Such an image can be useful if the system solicits feedback from the user. In one embodiment, the vision correction unit operates independently of the user, and may not generate an image for the user to view.

In one embodiment, a focus unit transmits an IR signal to the user's eye or eyes, 606. In one embodiment, the focus unit receives and processes reflections from the eye or eyes of the VR system user, 608. In one embodiment, the focus unit identifies a focus setting or a position of an adjustable lens, 610. If the received reflections indicate the image would not be focused for the user, 612 NO branch, the focus unit changes an adjustable optometry lens position, 614, and repeats the transmission of light and processing of reflections, 606, 608, 610. If the received reflections indicate the image would be focused for the user, 614 YES branch, in one embodiment, the optometry system maintains the optometry lens at the focused position, 616. In one embodiment, the optometry system adjusts the lens to the focused position and maintains it there while the user interacts with the VR system.

It will be understood that the vision correction unit will iterate at least a minimum number of times to determine a focused position. It will be understood that the process can be repeated separately for right and left eyes of the user. In one embodiment, once the optics are positioned in a way to provide a clear visual experience for the user, the VR system initiates the VR experience while applying the identified vision correction, 618.

In one aspect, an apparatus for a virtual reality (VR) interaction includes: a housing to position in front of the eyes of a user, the housing including a mount for a virtual reality image source to display images for the VR interaction; an adjustable lens; a focus unit to determine adjust a position of the adjustable lens with respect to the mount, to provide a vision-corrected image for a user.

In one embodiment, the adjustable lens comprises separate adjustable right and left lenses. In one embodiment, the focus unit is to provide separate right and left vision correction adjustments. In one embodiment, the adjustable lens comprises a lens of the housing to display the VR image. In one embodiment, the adjustable lens comprises a lens separate from a lens of the housing to display the VR image. In one embodiment, further comprising a dedicated virtual reality image source mounted in the mount. In one embodiment, the mount is to receive a mobile device as the virtual reality image source. In one embodiment, the focus unit includes an infrared (IR) source to transmit an IR signal towards a user's eyes, when worn by the user, and to adjust the adjustable lens in response to reflections of the IR signal from the user's eyes. In one embodiment, the focus unit is to automatically initiate a vision-correction adjustment in response to initiation of the VR interaction by the user. In one embodiment, the focus unit is to adjust a position of the adjustable lens in response to an input by the user. In one embodiment, the adjustable lens and the focus unit are included on an optometry unit mounted to the housing. In one embodiment, further comprising: a micro axis stepper motor to adjust the adjustable lens; and a motor driver to provide a control signal to the stepper motor. In one embodiment, the focus unit is to adjust the position of the adjustable lens to provide myopia vision correction. In one embodiment, the focus unit is to adjust the position of the adjustable lens to provide vision correction for myopia, hyperopia, amblyopia, presbyopia, or a combination.

In one aspect, a method for a virtual reality (VR) interaction includes: detecting a degree of myopia of a user of a VR system with an automatic optometry unit of the VR system; adjusting a position of a vision correction lens of the VR system to provide a vision-corrected image based on the degree of myopia detected.

In one embodiment, adjusting the position of the vision correction lens comprises adjusting the positions of separate right and left lenses. In one embodiment, adjusting the positions of the right and left lenses comprises adjusting the separate right and left lenses by different amounts. In one embodiment, the adjustable lens comprises a lens of the housing to display the VR image. In one embodiment, the adjustable lens comprises a lens separate from a lens of the housing to display the VR image. In one embodiment, adjusting the position of the vision correction lens comprises adjusting the position of the vision correction lens with respect to a dedicated virtual reality image source mounted in the VR system. In one embodiment, adjusting the position of the vision correction lens comprises adjusting the position of the vision correction lens with respect to a mobile device mounted in the VR system as a virtual reality image source. In one embodiment, detecting the degree of myopia comprises transmitting an infrared (IR) signal towards the user's eyes, and adjusting the vision correction lens in response to reflections of the IR signal from the user's eyes. In one embodiment, detecting the degree of myopia comprises automatically initiating a vision-correction adjustment in response to initiation of the VR interaction by the user. In one embodiment, adjusting the position of the vision correction lens comprises adjusting the position of the vision correction lens in response to an input by the user. In one embodiment, adjusting the position of the vision correction lens comprises providing a control signal to a micro axis stepper motor from a motor driver. In one embodiment, adjusting the position of the vision correction lens comprises adjusting the position of the adjustable lens to provide myopia vision correction. In one embodiment, adjusting the position of the vision correction lens comprises adjusting the position of the adjustable lens to provide vision correction for myopia, hyperopia, amblyopia, presbyopia, or a combination.

Flow diagrams as illustrated herein provide examples of sequences of various process actions. The flow diagrams can indicate operations to be executed by a software or firmware routine, as well as physical operations. In one embodiment, a flow diagram can illustrate the state of a finite state machine (FSM), which can be implemented in hardware and/or software. Although shown in a particular sequence or order, unless otherwise specified, the order of the actions can be modified. Thus, the illustrated embodiments should be understood only as an example, and the process can be performed in a different order, and some actions can be performed in parallel. Additionally, one or more actions can be omitted in various embodiments; thus, not all actions are required in every embodiment. Other process flows are possible.

To the extent various operations or functions are described herein, they can be described or defined as software code, instructions, configuration, and/or data. The content can be directly executable ("object" or "executable" form), source code, or difference code ("delta" or "patch" code). The software content of the embodiments described herein can be provided via an article of manufacture with the content stored thereon, or via a method of operating a communication interface to send data via the communication interface. A machine readable storage medium can cause a machine to perform the functions or operations described, and includes any mechanism that stores information in a form accessible by a machine (e.g., computing device, electronic system, etc.), such as recordable/non-recordable media (e.g., read only memory (ROM), random access memory (RAM), magnetic disk storage media, optical storage media, flash memory devices, etc.). A communication interface includes any mechanism that interfaces to any of a hardwired, wireless, optical, etc., medium to communicate to another device, such as a memory bus interface, a processor bus interface, an Internet connection, a disk controller, etc. The communication interface can be configured by providing configuration parameters and/or sending signals to prepare the communication interface to provide a data signal describing the software content. The communication interface can be accessed via one or more commands or signals sent to the communication interface.

Various components described herein can be a means for performing the operations or functions described. Each component described herein includes software, hardware, or a combination of these. The components can be implemented as software modules, hardware modules, special-purpose hardware (e.g., application specific hardware, application specific integrated circuits (ASICs), digital signal processors (DSPs), etc.), embedded controllers, hardwired circuitry, etc.

Besides what is described herein, various modifications can be made to the disclosed embodiments and implementations of the invention without departing from their scope. Therefore, the illustrations and examples herein should be construed in an illustrative, and not a restrictive sense.

What is claimed is:

1. An apparatus for a virtual reality (VR) interaction, comprising:
   a housing to position in front of a user's eyes, the housing including a mount for a virtual reality image source to display images for the VR interaction;
   separately adjustable right and left lenses; and
   a focus unit to automatically initiate a vision-correction adjustment measurement in response to initiation of the VR interaction by the user, including to separately adjust a position of the right lens and a position of the left lens with respect to the mount, to provide separate right vision and left vision correction adjustments image for a user, the focus unit including an infrared (IR) source to transmit an IR signal toward the user's eyes, when worn by the user, and to adjust the adjustable right and left lenses in response to measure reflections of the IR signal from the user's eyes to generate the vision-correction measurement in response to initiation of the VR interaction by the user, the focus unit to automatically initiate a vision-correction adjustment based on the vision-correction measurement, including to separately adjust a position of the right lens and a position of the left lens with respect to the mount.

2. The apparatus of claim 1, wherein the adjustable lens comprises a lens of the housing to display the VR image.

3. The apparatus of claim 1, wherein the adjustable lens comprises a lens separate from a lens of the housing to display the VR image.

4. The apparatus of claim 1, further comprising a dedicated virtual reality image source mounted in the mount.

5. The apparatus of claim 1, wherein the mount is to receive a mobile device as the virtual reality image source.

6. The apparatus of claim 1, wherein the adjustable lens and the focus unit are included on an optometry unit mounted to the housing.

7. The apparatus of claim 1, further comprising:
   a micro axis stepper motor to adjust the adjustable lens; and
   a motor driver to provide a control signal to the stepper motor.

8. The apparatus of claim 1, wherein the focus unit is to adjust the position of the adjustable lens to provide vision correction for myopia, hyperopia, amblyopia, presbyopia, or a combination.

9. The apparatus of claim 1, wherein the focus unit is to measure reflections of the IR signal including to measure how much IR light is captured from reflections from the user's eyes.

10. A method for a virtual reality (VR) interaction, comprising:
    detecting initiation of the VR interaction;
    automatically initiating a vision-correction measurement to detect a degree of myopia of eyes of a user of a VR system with an automatic optometry unit of the VR system in response to detection of initiation of the VR interaction by the user, including transmitting an infrared (IR) signal toward the user's eyes, when the VR system is worn by the user and measuring reflections of the IR signal from the user's eyes to generate the vision-correction measurement; and
    automatically initiating a vision-correction adjustment based on the vision correction measurement in response to the initiation of the VR interaction by the user, including separately adjusting a position of a left vision correction lens and a position of a right vision correction lens of the VR system to provide a vision-corrected image based on the degree of myopia detected.

11. The method of claim 10, wherein separately adjusting a position of a left vision correction lens and a position of a right vision correction lens comprises adjusting vision correction lenses that are separate from a lens of the VR system to display a VR image.

12. The method of claim 10, wherein adjusting the position of the vision correction lens comprises providing a control signal to a micro axis stepper motor from a motor driver.

13. The method of claim 10, wherein adjusting the position of the vision correction lens comprises adjusting the position of the adjustable lens to provide vision correction for myopia, hyperopia, amblyopia, presbyopia, or a combination.

14. The method of claim 10, wherein measuring the reflections of the IR signal comprises measuring how much IR light is captured from reflections from the user's eyes.

* * * * *